United States Patent [19]

Lew et al.

[11] Patent Number: 4,766,321

[45] Date of Patent: Aug. 23, 1988

[54] SYMBIOTIC FILTER-STERILIZER

[75] Inventors: Hyok S. Lew, 7890 Oak St., Arvada, Colo. 80005; Michael Stranahan, Woody Creek, Colo.

[73] Assignees: Jung G. Lew; Hyok S. Lew, both of Arvada, Colo.

[21] Appl. No.: 49,223

[22] Filed: May 13, 1987

Related U.S. Application Data

[63] Continuation-in-part of Ser. No. 866,893, May 27, 1986, Pat. No. 4,694,179.

[51] Int. Cl.$^4$ ............................................. G01N 21/01
[52] U.S. Cl. .................... 250/431; 250/436; 250/438; 422/24; 422/186.3; 210/760
[58] Field of Search .............. 250/431, 436, 437, 438; 422/24, DIG. 261, 186.1, 186.3; 210/260

[56] References Cited

U.S. PATENT DOCUMENTS

| | | | |
|---|---|---|---|
| 2,738,427 | 3/1956 | Wagon | 250/431 |
| 3,061,721 | 10/1962 | Brenner | 250/431 |
| 3,462,597 | 8/1969 | Young | 250/431 |
| 3,923,663 | 12/1975 | Reid | 422/24 |
| 4,033,719 | 7/1977 | Conn et al. | 250/437 |
| 4,087,925 | 5/1978 | Bienek | 250/437 |
| 4,141,830 | 2/1979 | Last | 422/24 |

OTHER PUBLICATIONS

"U.V./Ozone Cleaning of Surface", Vig et al., *IEEE Transaction on Parts, Hybrids, and Packaging*, vol. PHP-12, No. 4, Dec. 1976, pp. 365-370.

*Primary Examiner*—Bruce C. Anderson

[57] ABSTRACT

This invention discloses a combination of filters and germicidal ultraviolet lamps assembled in a symbiotic arrangement wherein the ultraviolet lamps have dual functions of sterilizing the fluid medium being filtered and preventing the filters from being clogged, while the filter enhances the germicidal effect of the ultraviolet light by creating uniform flow which evenly exposes the fluid medium to the ultraviolet light.

14 Claims, 2 Drawing Sheets

SYMBIOTIC FILTER-STERILIZER

BACKGROUND OF THE INVENTION

This patent application is a continuation-in-part to patent application Ser. No. 866,893 entitled "Symbiotic Filter-Sterilizer" filed on May 27, 1986 U.S. Pat. No. 4,694,179.

Traditionally, filters have been employed to filter suspended particles or dissolved ions out of a fluid medium while germicidal lamps such as ultraviolet lamps have been used to sterilize the liquid medium. In spite of the fact that the filters and the germicidal lamps have often been installed in many processing units which purify the fluid medium, these two elements have not been installed in a symbiotic arrangement wherein one element enhances the function of the other element while each element performs its own function unhindered by the dual role imposed by the symbiotic arrangement. While the manufacturing technology of the micro and ultra filters has scored a remarkable progress in recent years and a great variety of high quality filters have become available, the actual operation of filtration suffers badly from the problem of clogging of the filters. It is a shocking experience to discover that the ultraviolet lamps often installed next to the filters have been employed only to sterilize the fluid medium, when those ultraviolet lamps possess extraordinary capability of keeping the filters clean.

BRIEF SUMMARY OF THE INVENTION

The primary object of the present invention is to provide a symbiotic combination of filters and sterilizers, wherein the ultraviolet light sterilizing the fluid medium by direct germicidal action and by ozonizing also cleans the filters by oxidizing the organic matter clogging the pores of the filter, while the filters filtering out the suspended particles or dissolved ions enhances the germicidal action of the ultraviolet light by creating uniform flow of the fluid that evenly exposes the fluid medium to the ultraviolet light.

Another object is to provide a method for continuously cleaning the filters in place without interrupting the filtration operation.

A further object is to provide a method for cleaning filters without producing any by-products of cleaning such as a toxic waste solution.

Yet another object is to provide a symbiotic filter-sterilizer combination that includes means for cleaning the ultraviolet lamps or shield thereof without interrupting the filteration operation.

Yet a further object is to provide a symbiotic filter-sterilizer combination, which is economic and trouble-free in operation.

These and other objects of the present invention will become clear as the description thereof proceeds.

BRIEF DESCRIPTION OF THE FIGURES

The present invention may be described with a great clarity and specificity by referring to the following figures.

DESCRIPTION OF THE ILLUSTRATED EMBODIMENTS

Figure 1:
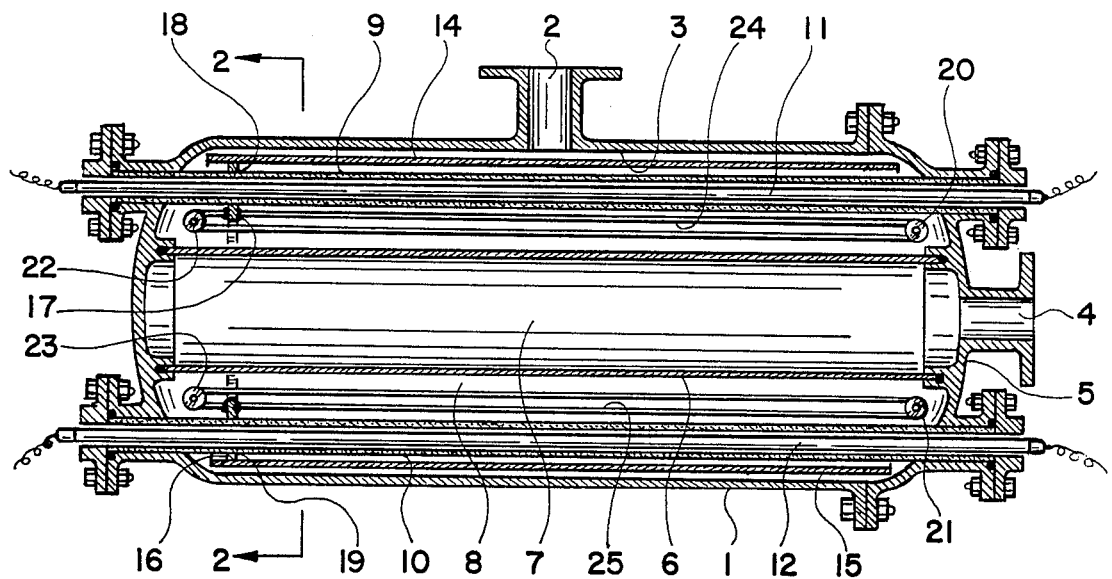
FIG. 1 illustrates a cross section of an embodiment of the symbiotic filter-sterilizer combination constructed in accordance with the principles of the present invention.

In FIG. 1 there is illustrated a cross section of an embodiment of the symbiotic filter-sterilizer assembled in accordance with the principles of the present invention, which cross section is taken along a plane including the central axis of the assembly. The cylindrical container vessel 1 with an inlet port 2 disposed through the cylindrical wall 3 and an outlet port 4 disposed through an end plate 5 includes a tubular filter 6 extending from one extremity to the other extremity of the container vessel 1. As the two ends of the tubular filter 6 are mated to the end plates of the container vessel 1, the interior of the container vessel 1 is divided into a cylindrical compartment 7 within the tubular filter 6 and an annular compartment 8 intermediate the tubular filter 6 and the cylindrical wall 3 of the container vessel 1. The outlet port 4 is open to the cylindrical compartment 7 within the tubular filter 6, while the inlet port 2 is open to the annular compartment 8. A plurality of transparent tubular shields 9, 10, etc. extending from one end plate to the other end plate of the container vessel 1 are disposed within the annular compartment 8 in an axisymmetric arrangement about the tubular filter 6, wherein the interiors of the transparent tubular shields are sealed off from the annular compartment 8. A plurality of elongated ultraviolet light sources 11, 12, etc. are respectively disposed within the transparent tubular shields 9, 10, etc. A plurality of elongated curved reflectors 14, 15, etc. partially enveloping the transparent tubular shields 9, 10. etc. direct the ultraviolet light from the ultraviolet lamps 11, 12, etc. towards the tubular filter 6. The interior surface of the cylindrical wall 3 of the container vessel 1 may be coated with an ultraviolet light reflecting lining to further direct the ultraviolet light towards the tubular filter 6. A wiper disc 16 with an oversized central hole 17 receiving the tubular filter 6 with a clearance is enclosed in the container vessel 1. The wiper disc 16 includes a plurality of holes 18, 19, etc. equipped with wiper rings, which holes are slidably engaged by the transparent tubular shields 9, 10, etc. The wiper disc 16 can be moved back and forth intermediate the two end discs of the container vessel 1 by rotating the drive pulleys 20, 21, etc., which pulleys together with the idler pulleys 22, 23, etc. move the closed loops of belts 24, 25, etc. anchored to the wiper disc 16. The shafts of the driver pulleys 20, 21, etc. extending through the wall of the container vessel 1 are driven by a common drive such as a hand-crank or reversible electric motor coupled to those shafts by gearing.

Figure 2:
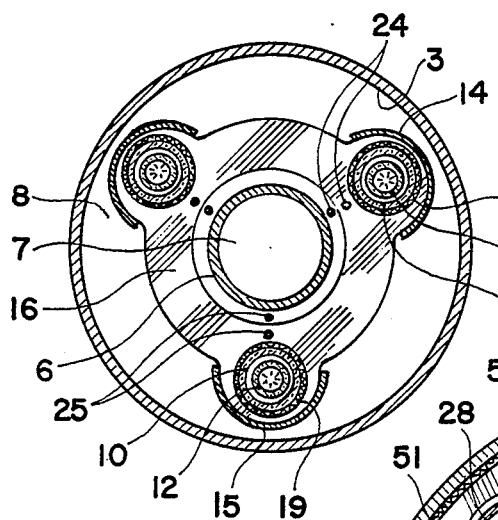
FIG. 2 illustrates another cross section of the embodiment shown in FIG. 1.

In FIG. 2 there is illustrated another cross section of the embodiment shown in FIG. 1, which cross section is taken along plane 2—2 as shown in FIG. 1. It is noticed that the wiper disc 16 is contoured in such a way that it wipes the reflecting surface of the reflectors 14, 15, etc. when the wiper disc 16 is moved back and forth in the axial direction. The outer perimeter of the wiper disc 16 may be modified to wipe the reflecting surface of the reflectors 14, 15, etc. as well as the interior surface of the cylindrical wall 3 of the container vessel when the interior surface of the cylindrical wall 3 is coated with an ultraviolet light reflecting lining.

The raw fluid medium to be filtered enters the container vessel 1 of the symbiotic filter-sterilizer through the inlet port 2. The fluid molecules permeate through the porous cylindrical wall 6 of the tubular filter, while the suspended particles or dissolved ions are retained in a concentration boundary layer within the annular compartment 8 adjacent to the exterior surface of the porous cylindrical wall of the tubular filter. The fluid medium entering through the inlet port 2 becomes spread uniformly over the exterior surface of the porous cylindrical wall of the tubular filter before permeating therethrough and, consequently, it becomes thoroughly exposed to the ultraviolet light from the germicidal lamps 11, 12, etc. The purified fluid medium filtered by the tubular filter 6 and sterilized by the ultraviolet light leaves through the outlet port 4. The ultraviolet light irradiating the exterior surface of the porous wall 6 of the tubular filter converts the dissolved oxygen in the fluid medium in the concentration boundary layer adjacent to the porous wall 6 to ozone. The ozone molecules produced by the ozonizing effect of the ultraviolet light oxidize organic materials clogging the pores of the porous wall 6 of the tubular filter. As a consequence, the ultraviolet light emitted from the germicidal lamps continuously cleans the tubular filters, while it sterilizes the fluid medium to be filtered. While the filter and the germicidal lamps respectively perform their original functions of filtering and sterilizing the fluid medium, they help one another to enhance their orginal functions as the germicidal lamps continuously clean the filter and the filter aids the sterilizing function of the germicidal lamps by uniformly exposing the fluid medium thereto. This is the exact reason why the combination of filters and germicidal lamps assembled in an arrangement as taught by the present invention is called the symbiotic filter-sterilizer. Of course, it is important to understand that the filters employed in a symbiotic filter-sterilizer must be made of ultraviolet light resistant materials such as flouro-carbons or ceramics or noncorroding sintered metal. If the fluid medium being filtered has insufficient amounts of dissolved oxygen, additional oxygen may be added to the fluid medium in order to attain the maximum cleaning of the filters by ozonizing. The solid particles or dissolved ions deposited on the exterior surface of the porous cylindrical wall of the tubular filter may be purged by back flushing, wherein the direction of the fluid flow through the symbiotic filter-sterilizer is reversed at a high flow rate.

Figure 3:
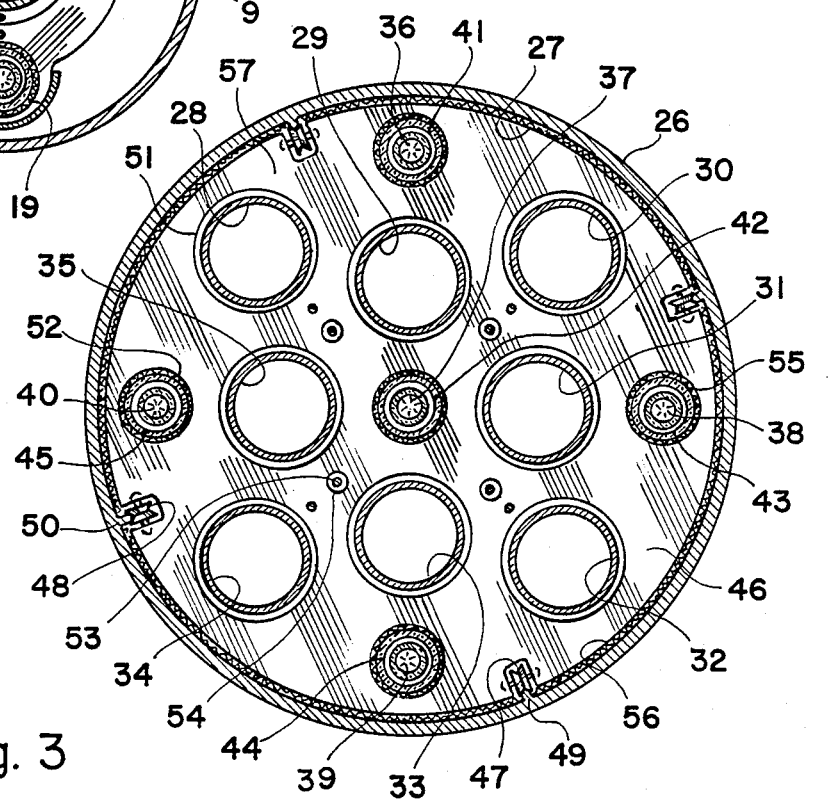
FIG. 3 illustrates a cross section of another embodiment of the symbiotic filter-sterilizer combination, which cross section is equivalent ot that shown in FIG. 2.

In FIG. 3 there is illustrates a cross section of another embodiment of the symbiotic filter-sterilizer of the present invention, which shows a cross section equivalent to that shown in FIG. 2. The container vessel 26 with the interior surface 27 of the cylindrical wall thereof coated with an ultraviolet light reflecting lining contains a plurality of tubular filters 28, 29, 30, 31, 32, 33, 34 and 35, and a plurality of elongated germicidal lamps 36, 37, 38, 39 and 40 disposed in a generally parallel relationship therebetween and in a mixed arrangement, wherein the exterior surfaces of all of the tubular filters are irradiated by the ultraviolet light directly emitted from the germicidal lamps or reflected from the ultraviolet light reflecting interior surface 27 of the container vessel wall 26. The plurality of germicidal lamps 36, 37, 38, 39 and 40 are respectively enclosed within a plurality of ultraviolet light transparent tubular shields 41, 42, 43, 44 and 45, which transparent tubular shields are arranged in a construction similar to the corresponding element shown in FIG. 1, wherein they provide a leak-proof protection for the germicidal lamps. The wiper disc 46 disposed perpendicular to the central axes of the tubular filters and the germicidal lamps is movable in directions parallel to the central axes of the tubular filters and the germicidal lamps as it is supported by a plurality of rollers 47, 48, etc. riding on rails 49, 50, etc. secured to the cylindrical wall 26 of the container vessel. The wiper disc includes a plurality of clearance holes 51 respectively engaged by the tubular filters in a free sliding relationship and a plurality of wiper holes 52 with wiper rings respectively engaged by the germicidal lamps in a rubbing relationship. The wiper disc 46 is moved back and forth between the two extremities of the container vessel by means of a plurality of closed loops of belts 53 extending through holes 54 disposed through the wiper disc 46, which closed loops of belts anchored to the wiper disc 46 are moved back and forth by the pulley driven by a hand crank or powered drive as illustrated in FIG. 1. It is a matter of design whether the wiper disc enclosed in the embodiment shown in FIG. 1 or 3 may be reciprocated by one or more telescoping rods extending from hydraulic or pneumatic actuators or by one or more cables operated by rodless hydraulic or pneumatic actuators. It should be mentioned that the transparent tubular shields are cleaned by the wiping action of the wiper rings 55 disposed along the circumference of the wiper holes 52, while the large wiper ring 56 disposed along the outer circumference of the wiper disc 46 cleans the ultraviolet light reflecting surfaces of the cylindrical wall 26 of the container vessel. An inlet port disposed through the wall of the container vessel such as the element 2 shown in FIG. 1 is open to the raw fluid compartment 57 intermediate the wall 26 of the container vessel and the porous walls of the tubular filters, while the interior spaces of the tubular filters are connected to an outlet port through plenum compartment or manifold of conduits. The particular pattern of allocating the germicidal lamps relative to the tubular filters shown in FIG. 3 is one of many readily available designs.

Figure 4:
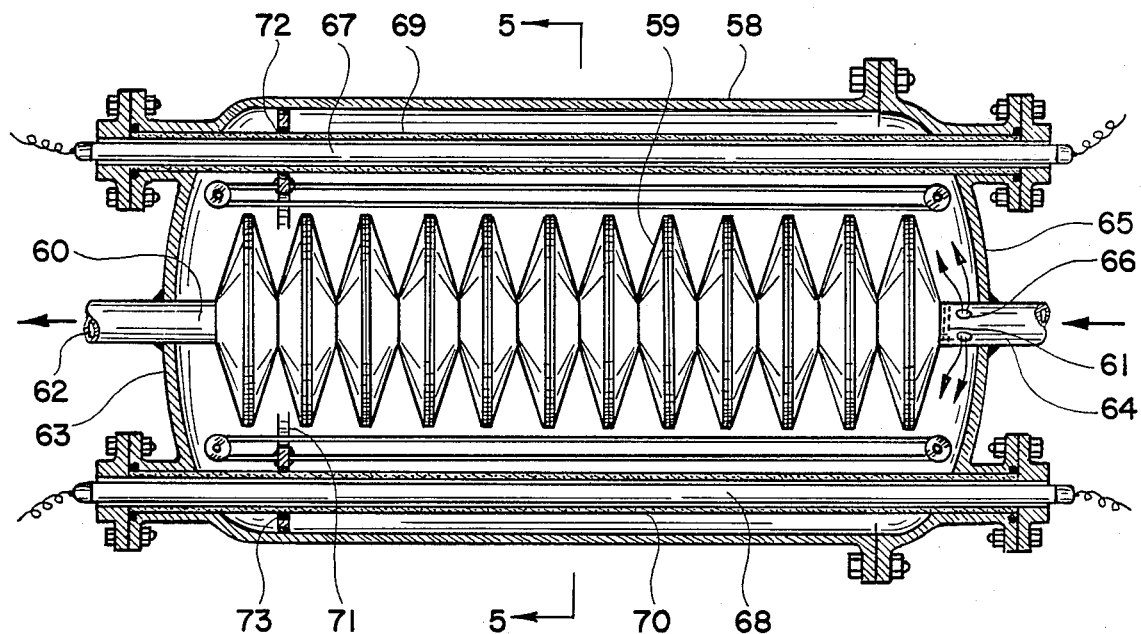
FIG. 4 illustrates a cross section of a further embodiment of the symbiotic filter-sterilizer combination of the present invention.

In FIG. 4 there is illustrated a cross section of a further embodiment of the symbiotic-filter of the present invention, which cross section is taken along a plane including the central axis of the assembly. The cylindrical container vessel 58 includes a plurality of leaf or disc filters 59 stacked in series, which are disposed within the container vessel 58 in a coaxial arrangement. The interior spaces of the leaf or disc filters 58 are connected to each other by the central conduit 60 extending from one extremity to the other extremity of the filter stack, which has a plurality of holes through the wall thereof over sections enclosed within the leaf or disc filters. One extremity 61 of the central conduit 60 is closed, while the other extremity 62 extending through the end plate 63 of the container vessel 58 is connected to an outlet port. The extension 64 of the central conduit extending from the closed end 61 extends through the end plate 65 of the container vessel 58 and is connected to an inlet port, which is open to the annular space intermediate the container vessel wall 58 and the assembly of the leaf or disc filters 59 by a plurality of holes 66 disposed through the wall of the extension 64 of the central conduit. A plurality of germicidal lamps 67, 68, etc. respectively enclosed in a plurality of the transparent tubular shields 69, 70, etc. are disposed within the container vessel 58 in a generally axisymmetric pattern about the assembly of the leaf or disc filters 59. The combinations of the germicidal lamps and the transparent tubular shields are arranged in the same way as the corresponding elements described in conjunction with FIG. 1. The wiper disc 71 of annular geometry includes a plurality of wiper holes 72, 73, etc. equipped with wiper rings receiving the transparent tubular shields in a sliding relationship, which wiper disc is moved back and forth between the two end plates 63 and 65 of the container vessel 58 by drive means described in conjunction with FIG. 3. The interior surface of the cylindrical wall of the container vessel 58 may be coated with an ultraviolet light reflecting lining in order to enhance the germicidal and filter cleaning role of the ultraviolet light emitted from the germicidal lamps 67, 68, etc.

Figure 5:
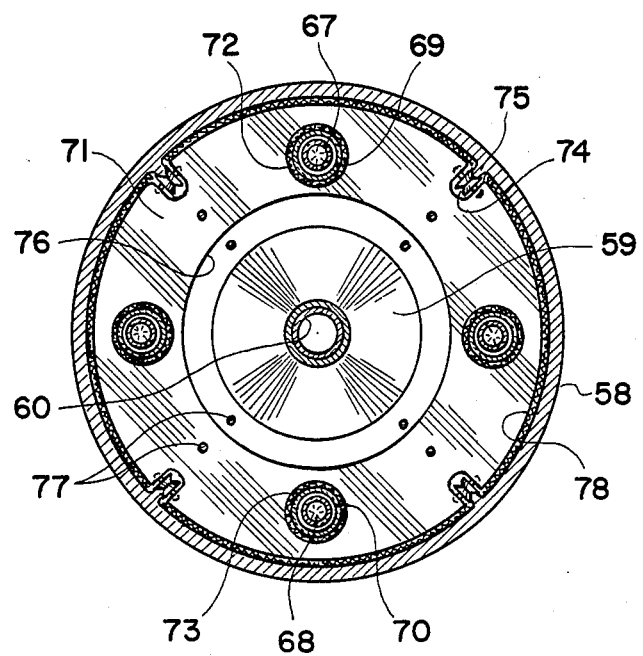
FIG. 5 illustrates another cross section of the embodiment shown in FIG. 4.

In FIG. 5 there is illustrated another cross section of the embodiment shown in FIG. 4, which cross section is taken along plane 5—5 as shown in FIG. 4. The annular wiper disc 71 is supported by a plurality of rollers 74 riding on a plurality of rails 75 secured to the cylindrical wall of the container vessel 58. The central opening 76 included in the wiper disc 71 receives the leaf or disc filter assembly with a clearance. The cables or belts 77 reciprocating the wiper disc 71 are routed through the gap intermediate the assembly of the leaf or disc filters and the annular wiper disc 71. The outer circumference of the annular wiper disc 71 includes a wiper ring 78 that wipes off the ultraviolet light reflecting interior surface of the cylindrical wall of the container vessel 58. It is clear that a symbiotic filter-sterilizer comprising a plurality of stacks of the leaf or disc filters may be assembled in an arrangement shown in FIG. 3 wherein the tubular filters 29, 30, 31, 32, 33, 34 and 35 are now replaced by the stack of leaf or disc filters.

While the principles of the present invention have now been made clear by the illustrative embodiments, there will be immediately obvious to those skilled in the art many modifications of the structures, arrangements, proportions, elements and materials which are particularly adapted to the specific working environments and operating conditions in the practice of the invention without departing from those principles.

We claim:

1. An apparatus for filtering and sterilizing fluid medium comprising in combination:
   (a) a container vessel including a first port and a second port;
   (b) at least one tubular filter with porous wall disposed within said container vessel wherein said first port is open to a first compartment intermediate wall of said container vessel and said tubular filter, and said second port is open to interior space of said tubular filter; and
   (c) at least one germicidal lamp disposed in said first compartment wherein germicidal electromagnetic radiation from said germicidal lamp transmits through fluid medium occupying said first compartment and irradiates porous wall of said tubular filter to break down by oxidation and radiation degrading particles clogging up the pores of said filter, while said filter enhances the sterilizing effect of said lamp by distributing the fluid flow for uniform exposure to the ultraviolet rays produced.

2. The combination as set forth in claim 1 wherein said combination includes one or more reflectors reflecting the germicidal electromagnetic radition back to the fluid medium in said first compartment and to the porous wall of said tubular filter.

3. The combination as set forth in claim 2 wherein said combination includes wiper means for cleaning said reflectors.

4. The combination as set forth in claim 1 wherein said germicidal lamp is enclosed within protective shield vessel with wall transparent to the germicidal electromagnetic radiation, wherein said protective shield vessel disposed within said first compartment isolates said germicidal lamp from the fluid in leak-proof manner.

5. The combination as set forth in claim 4 wherein said combination includes one or more reflectors reflecting the germicidal electromagnetic radiation back to the fluid medium in said first compartment and to the porous wall of said tubular filter.

6. The combination as set forth in claim 5 wherein said combination includes wiper means for cleaning said protective shield vessel and said reflectors.

7. An apparatus for filterring and sterilizing fluid medium comprising in combination:
   (a) a container vessel with at least one first port and at least one second port;
   (b) a plurality of tubular filters with porous wall disposed within said container vessel in a generally parallel arrangement wherein said first port is open to a first compartment intermediate wall of said container vessel and said plurality of tubular filters, and said second port is open to interior spaces of said plurality of tubular filters; and
   (c) a plurality of germicidal lamps disposed in said first compartment in generally parallel relationship with respect to said tubular filters in an arrangement wherein germicidal electromagnetic radiation from said germicidal lamps transmits through fluid medium occupying said first compartment and irradiates porous walls of said tubular filters to break down by oxidation and radiation degrading particles clogging up the pores of said filters, while said filters enhance the sterilizing effect of said lamps by distributing the fluid flow for uniform exposure to the ultraviolet rays produced.

8. The combination as set forth in claim 7 wherein said germicidal lamps are respectively enclosed within a plurality of protective shield vessels with walls transparent to the germicidal electromagnetic radiation, wherein said protective shield vessels disposed within said first compartment isolate said germicidal lamps from the fluid in leak-proof manner.

9. The combination as set forth in claim 8 wherein said combination includes one or more reflectors reflecting the germicidal electromagnetic radiation back to the fluid medium in said first compartment and to porous walls of said tubular filters.

10. The combination as set forth in claim 9 wherein said combination includes wiper means for cleaning said protective shield vessels and said reflectors.

11. An apparatus for filtering and sterilizing fluid medium comprising in combination:
    (a) a container vessel with at least one first port and at least one second port;
    (b) a plurality of disc filters assembled into at least one stacked assembly, said stacked assembly of the disc filters disposed within said container vessel wherein said first port is open to a first compartment intermediate wall of said container vessel and said stacked assembly of disc filters, and said second port is open to interior spaces of said plurality of disc filters; and (c) a plurality of germicidal lamps disposed in said first compartment about said stacked assembly of the disc filters wherein germicidal electromagnetic radiation from said germicidal lamps transmits through fluid medium occupying said first compartment and irradiates surfaces of said disc filters to break down by oxidation and radiation degrading particles clogging up the pores of said filters, while said filters enhance the sterilizing effect of said lamps by distributing the fluid flow for uniform exposure to the ultraviolet rays produced.

12. The combination as set forth in claim 11 wherein said germicidal lamps are respectively enclosed within a plurality of protective shield vessels with walls transparent to the germicidal electromagnetic radiation, wherein said protective shield vessels disposed within said first compartment isolate said germicidal lamps from the fluid in leak-proof manner.

13. The combination as set forth in claim 12 wherein said combination includes one or more reflectors reflecting the germicidal electromagnetic radiation back to the fluid medium in said first compartment and to surfaces of said disc filters.

14. The combination as set forth in claim 13 wherein said combination includes wiper means for cleaning said protective shield vessels and said reflectors.

* * * * *